(12) United States Patent
Grimme et al.

(10) Patent No.: US 9,952,878 B2
(45) Date of Patent: Apr. 24, 2018

(54) SYSTEM WITH A MEDICAL APPARATUS, AND METHOD FOR CONTROLLING STARTUP AND SHUTDOWN OF THE SYSTEM

(71) Applicant: Siemens Healthcare GmbH, Erlangen (DE)

(72) Inventors: Andreas Grimme, Erlangen (DE); Rolf Heinrichs, Roettenbach (DE); Ludwig Kreischer, Dormitz (DE); Andreas Schmidt, Erlangen (DE)

(73) Assignee: Siemens Healthcare GmbH, Erlangen (DE)

( * ) Notice: Subject to any disclaimer, the term of this patent is extended or adjusted under 35 U.S.C. 154(b) by 96 days.

(21) Appl. No.: 15/216,749

(22) Filed: Jul. 22, 2016

(65) Prior Publication Data

US 2017/0024220 A1    Jan. 26, 2017

(30) Foreign Application Priority Data

Jul. 23, 2015    (DE) ........................ 10 2015 213 941

(51) Int. Cl.
  *H04L 12/12*    (2006.01)
  *G06F 9/44*     (2018.01)
  *A61B 6/00*     (2006.01)
  *A61B 8/00*     (2006.01)
  *G06F 19/00*    (2018.01)

(52) U.S. Cl.
  CPC .............. *G06F 9/4401* (2013.01); *A61B 6/56* (2013.01); *A61B 8/56* (2013.01); *G06F 9/442* (2013.01); *G06F 19/30* (2013.01); *H04L 12/12* (2013.01)

(58) Field of Classification Search
  CPC .............. A61B 6/56; A61B 8/56; H04L 12/12
  See application file for complete search history.

(56) References Cited

U.S. PATENT DOCUMENTS

| | | | |
|---|---|---|---|
| 6,198,285 B1 | 3/2001 | Kormos et al. | |
| 2008/0012833 A1 | 1/2008 | Beck et al. | |
| 2009/0060136 A1* | 3/2009 | Tamakoshi | G03B 42/021 378/91 |
| 2009/0150691 A1* | 6/2009 | Chen | G06F 1/3209 713/310 |
| 2016/0143602 A1* | 5/2016 | Hiroike | A61B 6/463 378/98.5 |

* cited by examiner

*Primary Examiner* — Albert Wang
(74) *Attorney, Agent, or Firm* — Schiff Hardin LLP

(57) ABSTRACT

In a system and operating method wherein the system includes a medical apparatus and an operator console, a first input processor is assigned to the operator console and acquires a shutdown command that triggers a shutdown operation of the operator console, and a second input processor is assigned to the medical apparatus and acquires a startup command that triggers a startup operation of the medical device. A first interface forwards the shutdown command from the operator console to the medical apparatus wherein a shutdown operation of the medical apparatus is triggered, and a second interface forwards the startup command from the medical apparatus to the operator console, wherein a startup operation of the operator console is triggered.

10 Claims, 3 Drawing Sheets

SYSTEM WITH A MEDICAL APPARATUS, AND METHOD FOR CONTROLLING STARTUP AND SHUTDOWN OF THE SYSTEM

BACKGROUND OF THE INVENTION

Field of the Invention

The invention concerns a system, and a method for controlling the system and a non-transitory, computer-readable data storage medium for implementing such a method.

Description of the Prior Art

Medical apparatuses, in particular large medical appliances and/or medical imaging apparatuses, are typically connected for data exchange purposes to an operator console that enables the medical apparatus to be operated and controlled by a user.

SUMMARY OF THE INVENTION

An object of the invention is to enable a coordinated startup and shutdown operation of the medical apparatus and of the operator console that are combined in a system.

The system according to the invention has a medical apparatus, and an operator console that enables the medical apparatus to be operated and controlled by a user.

A first input unit is assigned to the operator console and is designed to acquire a shutdown command that triggers a shutdown operation of the operator console.

A second input unit is assigned to the medical apparatus and is designed to acquire a startup command that triggers a startup operation of the medical apparatus.

A first interface which is designed to forward the shutdown command acquired by the first input unit from the operator console to the medical apparatus, and the shutdown command forwarded to the medical apparatus triggers a shutdown operation of the medical apparatus.

A second interface which is designed to forward the startup command acquired by the second input unit from the medical apparatus to the operator console, and the startup command forwarded to the operator console triggers a startup operation of the operator console.

The medical apparatus is separate from the operator console. A spatial separation exists between the medical apparatus and the operator console, as described in detail below. The medical apparatus and the operator console accordingly have separate control units, which are implemented in particular in the form of separate computing systems. The medical apparatus and the operator console, in particular the separate computing systems of the medical apparatus and the operator console, are connected to one another for the purpose of exchanging control commands via the first interface and the second interface.

The operator console, also known as a control computer, typically provides input elements for the user which facilitates the operation and control of the medical apparatus, for example when controlling an examination and/or treatment of a patient by operation of the medical apparatus. Typically, the operator console additionally provides output elements for the user that can provide information about the status of the examination and/or treatment of the patient by the medical apparatus. Thus, the operator console can include a monitor having a user interface for operating and controlling the medical apparatus.

The first interface is embodied as a data interface that can transfer data from the operator console to the medical apparatus. The second interface is embodied in particular as a data interface which can transfer data from the medical apparatus to the operator console. In this case the first interface and the second interface can be virtual interfaces realized as program logic and/or physical hardware interfaces. In an embodiment of the first interface and second interface as hardware interfaces, a spatial arrangement of the first interface and the second interface can in this case be chosen in particular as deemed appropriate.

The first input unit can then be a part of the user interface, embodied as a button on the user interface, for example. It is also possible for the first input unit to be embodied as a physical switch that can be pressed by the user. In that case, the physical switch is arranged on the operator console, embodied as part of the operator console, for example. The first input unit preferably is located in the room in which the operator console is also located, i.e. in a control room. Other embodiments and/or arrangements of the first input unit considered beneficial by those skilled in the art can also be implemented.

The second input unit is a component of the medical apparatus. The second input unit can be arranged in the same room as the medical apparatus, i.e. in an equipment room. It is also possible for the second input unit to be arranged spatially separated from the medical apparatus. For example, the second input unit can also be arranged in the control room in which the operator console is located, but the second input unit is always arranged separated from the first input unit, preferably at a relatively large spatial distance from the first input unit. The second input unit can be embodied as a button of a user interface that is assigned to the medical apparatus, but the second input unit is not arranged on the user interface of the operator console. Preferably, the second input unit is formed by a physical switch. The assignment of the second input unit to the medical apparatus can be implemented by the second input unit being connected directly to the medical apparatus, in particular to the control computer of the medical apparatus, for the purposes of a data exchange. Other embodiments and/or arrangements of the second input unit considered beneficial by those skilled in the art can also be implemented.

The first input unit is connected to the operator console or integrated into the operator console such that an actuation of the first input unit directly triggers a shutdown of the operator console. Thus, a shutdown operation of the operator console can be initiated as soon as the first input unit has been actuated, in particular by a user. During this shutdown operation, a sequence referred to as a shutdown sequence of the operator console can be performed. This shutdown sequence can include, for example, installation of a more recent version of an item of software (a software update) of the operator console and/or a cleanup of temporary files and/or a shutdown of the operating system of the operator console. Subsequently, the computer of the operator console can perform a self-shutdown, whereupon the operator console switches into a mode known as a soft-off state, as described in detail below.

After the actuation of the first input unit has been detected, the shutdown command is relayed automatically to the medical apparatus. The shutdown command can be relayed in the form of a shutdown instruction from the operator console to the medical apparatus. On the basis of the received shutdown command, powering-down, including disconnection from a power supply, of the medical apparatus can then be initiated automatically. In this way the actuation of the first input unit can initiate the simultaneous shutdown of the operator console and of the medical apparatus. Advantageously, no separate shutdown of the operator console and of the medical apparatus, respectively, is necessary. In this way, the operating sequence for shutting down the operator console and the medical apparatus can be simplified. The user no longer has to wait for the medical apparatus to be in a safe state during the shutdown before the medical apparatus can be disconnected from the power supply via a master switch. With the inventive method, the operator console and the medical apparatus can be powered-down in a mutually coordinated and fully automated manner following just the once-only actuation of the first input unit. Since the shutdown of the medical apparatus and of the operator console can be carried out in an unsupervised manner in this way, time-consuming computing operations, such as software updates, can be performed during the shutdown operation of the operator console.

In this case the shutdown operation of the operator console and the shutdown operation of the medical apparatus can be performed simultaneously or in time-staggered fashion. The shutdown operation of the operator console and the shutdown operation of the medical apparatus can be coordinated with one another such that initially the medical apparatus will be disconnected from the power supply and then the operator console will perform a self-shutdown, or switch to a sleep state. This enables an implementation of an expensive proprietary shutdown logic of the medical apparatus to be avoided, since the computer of the operator console can at least partially take over the control of the shutdown operation of the medical apparatus.

According to the invention, the startup, in particular the restart, of the operator console and of the medical apparatus is also intended to be performed by a single user interaction, namely the actuation of the second input unit, analogously to the switching-off of the operator console and of the medical apparatus. For this purpose, the second input unit is connected to the medical apparatus or integrated into the medical apparatus such that an actuation of the second input unit directly triggers a startup of the medical apparatus. Thus, a startup operation of the medical apparatus can be initiated as soon as the second input unit has been actuated, in particular by a user. To that end the second input unit can act directly on a controller of the power supply of the medical apparatus such that an actuation of the second input unit activates the power supply of the medical apparatus.

After the actuation of the second input unit has been detected, the startup command is relayed automatically to the operator console. On the basis of the received startup command, a startup or a powering-up of the operator console can then be initiated automatically. In this case the startup operation of the operator console can also include an awakening of the operator console ("wake up") from a sleep state. In this way the actuation of the second input unit can advantageously initiate the simultaneous startup of the operator console and of the medical apparatus. Advantageously, no separate startup of the operator console and of the medical apparatus is necessary. In this way an operating sequence for starting up the operator console and the medical apparatus can be simplified. The actuation of the second input unit, which triggers the startup of the medical apparatus and of the operator console, is initiated in this case following a termination of the shutdown operation of the medical apparatus and of the operator console. The startup of the medical apparatus and of the operator console can thus represent a restart of the medical apparatus and of the operator console. The operator console and the medical apparatus are in this case switched on in synchronization with one another, as described in detail below.

The inventive system thus provides an initiation or a control of a startup operation of the system from a different system than an initiation or a control of a shutdown operation of the system. The startup operation of the system, in particular the startup operation of the operator console and of the medical apparatus, is initiated by the medical apparatus, in particular through actuation of the second input unit of the medical apparatus. Conversely, the shutdown operation of the system, in particular the shutdown operation of the operator console and of the medical apparatus, is initiated by the operator console, in particular through an actuation of the first input unit of the operator console. This enables long waiting times for a user to be avoided when the system is switched on and/or switched off. Such long waiting times when a system component is switched off impact the system as a whole by precluding use thereof, for examining patients, which is uneconomical for the clinic or hospital in which the medical apparatus is situated. The inventive system can enable a waiting time saving in the order of several minutes, for example between 10 and 15 minutes. The switch-on operation and the switch-off operation are thus intended as a mutual coordination of the medical apparatus and of the operator console. A complex and expensive startup and shutdown controller, which is installed separately for the medical apparatus and for the operator console, and which therefore leads to additional hardware costs, can be dispensed with in this way. At the same time, the operating sequence during the switching-on and switching-off of the system can be simplified and/or accelerated.

As noted, the medical apparatus and the operator console are arranged spatially separated from one another such that the medical apparatus is located in an equipment room and the operator console is located in a control room. The medical apparatus preferably is situated entirely in the equipment room. The operator console preferably is situated entirely in the control room. The equipment room and the control room are usually adjacent rooms in a hospital or a medical practice. The equipment room and the control room can be spatially isolated from one another. The operation and control of the medical apparatus can then be performed by a user from the control room via the operator console. Thus, the first input unit is located in the control room. The second input unit can be located in the equipment room, such as directly next to the medical apparatus. Alternatively, the second input unit can also be located in the control room, in which case there then exists a direct connection to the medical apparatus.

In an embodiment, the medical apparatus has a control computer that controls the medical apparatus, and the first interface is designed to forward the shutdown command acquired by the first input unit from the operator console to the control computer of the medical apparatus. In the same way, the startup command can also be transferred by the second input unit directly to the control computer of the medical apparatus. In this case the control computer can be designed to have multiple levels, i.e. the shutdown command can be relayed between multiple parts of the control computer in order, for example, to allow the multiple parts of the control computer to be powered down separately. The control computer can be embodied in particular for controlling the hardware of the medical apparatus.

In another embodiment, the control computer is located in the equipment room. Accordingly, the control computer can be located directly in the same room as the medical apparatus. The control computer can be integrated into a hardware component of the medical apparatus and in this way constitute a part of the hardware of the medical apparatus. The control computer thus can be embodied as physically decoupled from the operator console, which is situated in the control room.

In another embodiment, the shutdown operation of the medical apparatus includes a disconnection of the medical apparatus from a power supply of the medical apparatus, wherein the disconnection from the power supply is initiated by the control computer as a function of the shutdown command forwarded to the control computer. The disconnection from the power supply can in this case include a disconnection of the medical apparatus from a line voltage. The disconnection from the power supply can thus be initiated by an internal computing component of the medical apparatus. In this case, however, the disconnection from the power supply is initiated by the actuation of the first input unit of the operator console. The control computer of the medical apparatus thus does not trigger the disconnection from the power supply on its own initiative, but acts as a function of the shutdown command transferred from the operator console to the control computer. The coordination of the shutdown operation of the medical apparatus can in this case be handled by the control computer, or by an arithmetic logic device of the operator console. Accordingly, the control computer of the medical apparatus can be implemented without a dedicated shutdown controller, or by a simple inexpensive controller which initiates the disconnection of the medical apparatus from the power supply as a function of the received shutdown command.

In another embodiment, the shutdown operation of the operator console includes placing the operator console into a soft-off state. In the soft-off state, the operator console is switched off or in a sleep state. In the soft-off state, the operator console is still connected to line voltage. The soft-off state thus can enable a simple restart or wake-up of the operator console as a function of the startup command forwarded to the operator console.

In another embodiment, the second interface is designed as a network interface between the medical apparatus and the operator console, the startup operation of the operator console being triggered by means of a Wake-on-LAN method. For that purpose the operator console was placed in particular into a soft-off state during the shutdown. In this way the second interface can forward the startup command from the medical apparatus to the operator console via a network connection. For the Wake-on-LAN method, the startup command can in this case be embodied as a dedicated data packet or as a change to a carrier connection. The second interface is designed as an Ethernet interface, the Wake-on-LAN startup command being transferred from the medical apparatus to the operator console via an Ethernet protocol. The startup of the operator console can in this case comprise an awakening of the computer of the operator console from the sleep state, namely the soft-off state, to an operating state. The second interface can also be designed as a different type of interface, as a serial interface for example.

In another embodiment, the second interface is designed such that the startup operation of the medical apparatus and the startup operation of the operator console run concurrently. For that purpose, the startup operation of the medical apparatus and the startup operation of the operator console can start with only a small delay and/or simultaneously. In this way the startup operation of the medical apparatus and the startup operation of the operator console can run in synchronization with one another over at least a certain period of time. For that purpose the second interface can advantageously relay the startup command to the operator console immediately after the actuation of the second input unit in time. The second interface can thus forward the startup command in such a way that the startup operation of the medical apparatus and the startup operation of the operator console run concurrently. Furthermore, a time saving can be achieved by the simultaneous startup of the medical apparatus and of the operator console and the system can be in an operationally ready state more quickly. A further speedup of the operating sequences can be achieved as a result.

The inventive method for controlling a system having a medical apparatus and an operator console for operating and controlling the medical apparatus, has the following steps.

A shutdown command is acquired by a first input unit assigned to the operator console.

A shutdown operation of the operator console is triggered as a function of the acquired shutdown command.

The shutdown command is forwarded from the operator console to the medical apparatus, wherein a shutdown operation of the medical apparatus is triggered.

A startup command is acquired by a second input unit assigned to the medical apparatus following termination of the shutdown operation of the operator console and of the medical apparatus.

A startup operation of the medical apparatus is triggered as a function of the acquired startup command.

The startup command is forwarded from the medical apparatus to the operator console, wherein a startup operation of the operator console is triggered.

The method can be executed in accordance with a time sequence as described above. Thus, for example, the shutdown operation of the operator console can be timed to terminate later than the shutdown operation of the medical apparatus. The startup operation of the medical apparatus and of the operator console is preferably performed at least partially in synchronization with one another.

The invention also encompasses a non-transitory, computer-readable data storage medium that can be loaded directly into a memory of a programmable computer of a system as described above, and that is encoded with program code that cause the computer to operate the system in order to implement the method according to the invention as described above.

In this regard the computer must fulfill certain prerequisites, such as having a suitable random access memory, a suitable graphics card or a suitable logic unit, for example, so that the method steps can be performed efficiently.

Examples of electronically readable data media are a DVD, a magnetic tape or a USB stick on which electronically readable control information is stored.

The advantages of the inventive method and of the inventive storage medium substantially correspond to the advantages of the inventive system as explained. Features, advantages and alternative embodiments cited above are applicable to the other aspects of the invention. The functional features of the method are embodied by corresponding physical modules, in particular by hardware modules.

DESCRIPTION OF THE PREFERRED EMBODIMENTS

Figure 1:
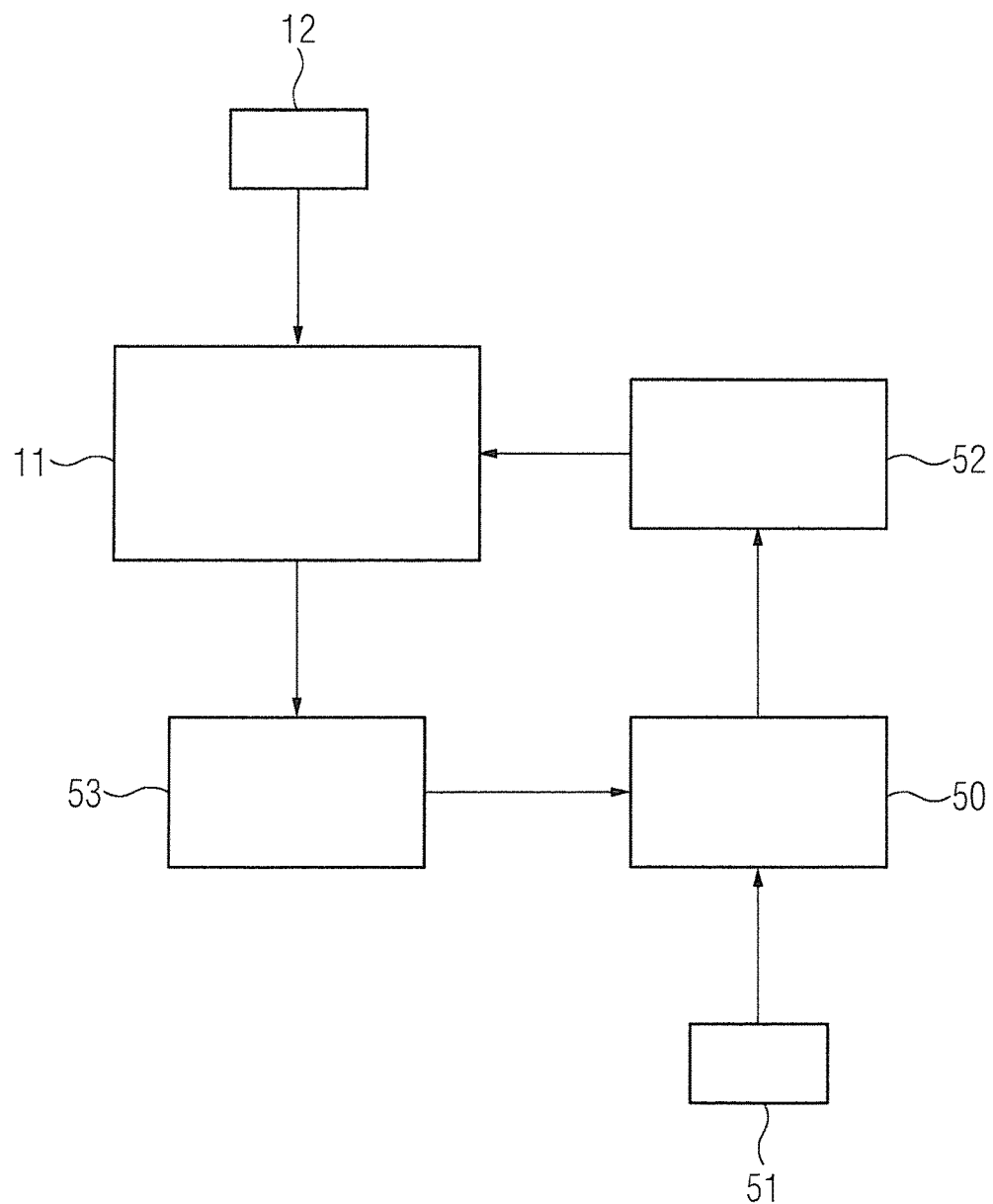
FIG. 1 shows a first embodiment of the system according to the invention.

FIG. 1 shows a first embodiment variant of the system according to the invention.

The system has a medical apparatus 11, in particular a large medical appliance. The medical apparatus 11 can be embodied as a medical imaging apparatus. For example, the medical imaging apparatus can be a magnetic resonance apparatus, a single-photon emission tomography (SPECT) apparatus, a positron emission tomography (PET) apparatus, a computed tomography apparatus, an ultrasound apparatus, an X-ray apparatus or a C-arm apparatus. Also possible in this context are combined medical imaging apparatuses formed by any combination composed of the aforementioned imaging modalities. Other medical apparatuses which are not medical imaging devices are also conceivable. The medical apparatus 11 can be a treatment apparatus. Thus, the medical apparatus 11 can alternatively be embodied as an apparatus for intensive medicine, for example as a mobile monitoring device and/or respiratory device and/or infusion device and/or dialysis device. Furthermore, the medical apparatus 11 can be embodied as a radiotherapy device. The medical apparatus 11 can be embodied as a lithotripsy device. The medical apparatus 11 can also be embodied as a cardiological diagnostic device, as an ECG device. It is also conceivable for the medical apparatus 11 to be an interventional treatment device for performing an interventional procedure. Other medical apparatuses considered beneficial by those skilled in the art can also be implemented.

The medical apparatus 11 is assigned a second input unit 12 that is designed to acquire a startup command. The startup command triggers a startup operation of the medical apparatus 11.

The system further has an operator console 50 that enables the medical apparatus 11 to be operated and controlled by a user. The operator console 50 is assigned a first input unit 51 that is designed to acquire a shutdown command. The shutdown command triggers a shutdown operation of the operator console 50.

The system further has a first interface 52 and a second interface 53. The first interface 52 is designed to forward the shutdown command acquired by the first input unit 51 from the operator console 50 to the medical apparatus 11. The shutdown command forwarded to the medical apparatus 11 triggers a shutdown operation of the medical apparatus 11. The second interface 53 is designed to forward the startup command acquired by the second input unit 12 from the medical apparatus 11 to the operator console 50. The startup command forwarded to the operator console 50 triggers a startup operation 50 of the operator console.

Figure 2:
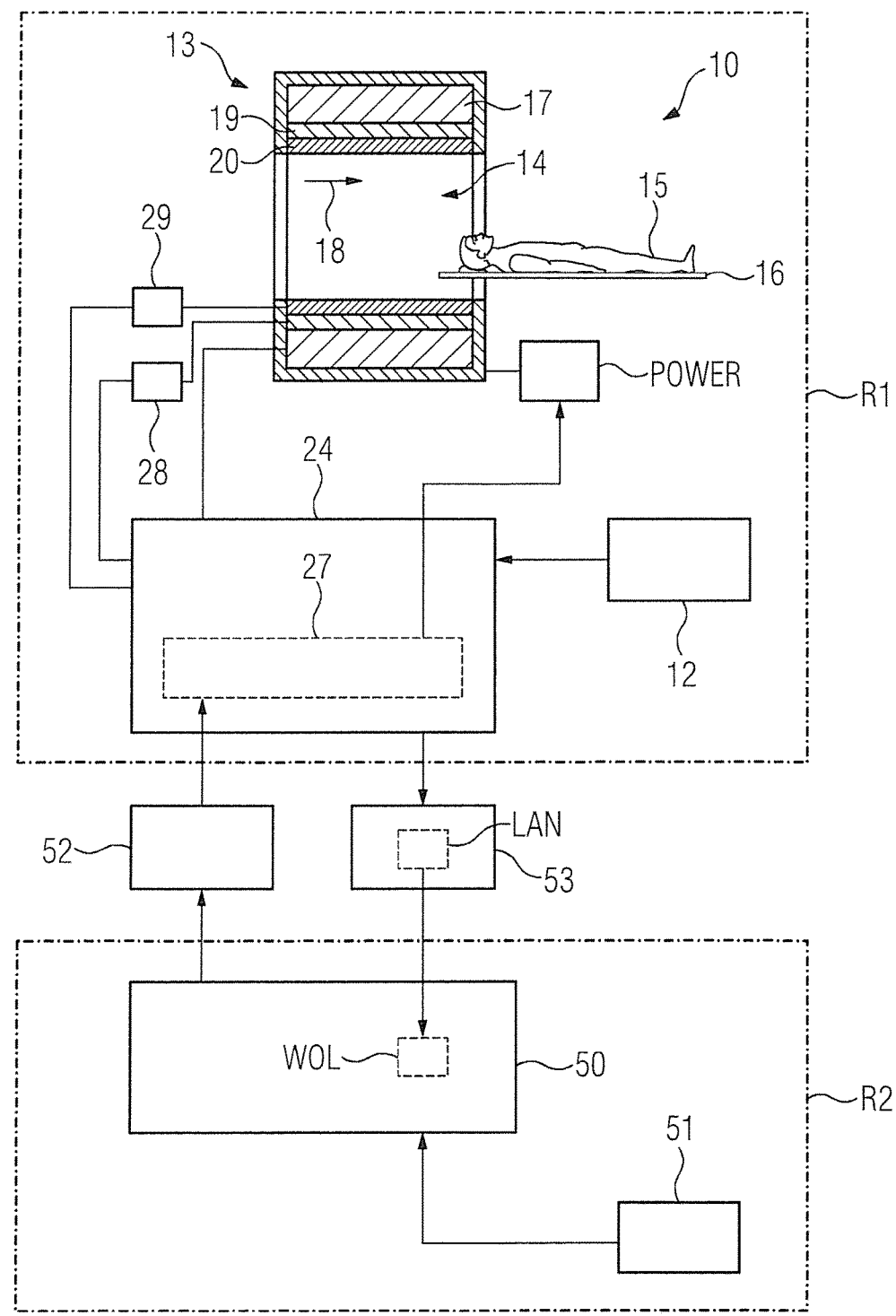
FIG. 2 shows a second embodiment of the system according to the invention.

FIG. 2 shows a second embodiment variant of a system according to the invention. An alternative embodiment of the system to that represented in FIG. 1 is shown in FIG. 2. The following description limits itself essentially to the differences compared to the exemplary embodiment in FIG. 1, with reference being made to the description of the exemplary embodiment in FIG. 1 in respect of components, features and functions that remain the same. Components, features and functions that remain substantially the same are labeled consistently with the same reference numerals In the embodiment of FIG. 2, the medical apparatus 11 is a magnetic resonance apparatus 10 as an example. The medical apparatus 11 can also be embodied differently, as described in FIG. 1, for example.

The magnetic resonance apparatus 10 has a magnetic resonance scanner 13 having a basic field magnet 17 for generating a strong and constant basic magnetic field 18. In addition, the scanner 13 has a cylinder-shaped patient receiving zone 14 for receiving an examination subject 15, in the present case a patient, the patient receiving zone 14 being cylindrically enclosed by the scanner 13 in a circumferential direction. The patient 15 can be introduced into the patient receiving zone 14 by a patient support 16 of the magnetic resonance scanner 13. For this purpose, the patient support 16 has a patient transport table that is movable within the scanner 13.

The scanner 13 additionally has a gradient coil arrangement 19 for generating magnetic field gradients that are used for spatial encoding during an imaging session. The gradient coil arrangement 19 is driven by a gradient control processor 28. The scanner 13 furthermore has a radio-frequency (RF) antenna 20, which in the case shown is embodied as a body coil permanently integrated in the magnetic resonance scanner 13, and a radio-frequency antenna control processor 29. The radio-frequency antenna 20 is driven by the radio-frequency antenna control processor 29 so as to radiate radio-frequency magnetic resonance sequences into an examination chamber which is substantially formed by the patient receiving zone 14. The radio-frequency sequence excites nuclear spins in the examination subject 15, so as to cause the excited nuclear spins to deviate from the polarization produced by the basic magnetic field 18, so as to emit magnetic resonance signals as the nuclear spins relax from this excitation. The radio-frequency antenna 20 is furthermore designed to receive the magnetic resonance signals from the patient 15.

The magnetic resonance apparatus 10 has a control computer 24 that controls the basic field magnet 17, the gradient control processor 28 and the radio-frequency antenna control processor 29. The control computer 24 is responsible for the centralized control of the magnetic resonance apparatus 10, such as performing a predetermined imaging gradient echo sequence. The control computer 24 can include the gradient control processor 28 and/or the radio-frequency antenna control processor 29. In the case shown, the control computer 24 has a shutdown controller 27. The shutdown controller 27 can switch a central power supply POWER of the magnetic resonance apparatus 10 on and off, which central power supply POWER supplies the scanner 13 and other components with electric current. In a typical application case the control computer 24 will have further subcomponents for controlling the magnetic resonance apparatus 10.

The illustrated magnetic resonance apparatus 10 can of course have further components that are normally included in such apparatuses. The general operation of a magnetic resonance apparatus 10 is known to those skilled in the art, so a detailed description of the further components is not necessary herein.

In the case shown, the magnetic resonance apparatus 10 is located in an equipment room R1. In the case shown, the control computer 24 is also located in the equipment room R1 together with the magnetic resonance apparatus 10. The operator console 50 is located spatially separated from the magnetic resonance apparatus 10 in a control room R2 together with the first input unit 51. It is also conceivable for the first input unit 51 and/or the second input unit 12 to be arranged in a different location from the case shown in FIG. 2.

As an example, with the system in the running system state, a user is now to trigger a shutdown of the system at the operator console 50 or, as the case may be, at the first input unit 51, which is assigned to the operator console 50. To that end, the user can for example press a "Power Off" button, which then forms the first input unit 51, on a user interface of the operator console 50. The user can then leave the control room R2, because the remainder of the shutdown operation of the system can execute fully automatically.

In the case shown in FIG. 2, the first interface 52 is embodied specifically for forwarding the shutdown command acquired by the first input unit 51 from the operator console 50 to the control computer 24 of the magnetic resonance apparatus 10. In the case shown, the shutdown command is forwarded in the control computer, possibly with a programmed delay, to the shutdown controller 27. The shutdown controller 27 can then generate a control signal, via an alarm box for example, which control signal switches a power distributor into a standby state. In this way all of the components of the magnetic resonance apparatus 10, although in particular initially not the operator console 50, can be disconnected from the power supply POWER, in particular from the line voltage. To sum up, the shutdown operation of the magnetic resonance apparatus 10 can thus entail a disconnection of the magnetic resonance apparatus 10 from a power supply POWER of the magnetic resonance apparatus 10. The disconnection from the power supply POWER is in this case initiated by the control computer 24 as a function of the shutdown command forwarded to the control computer 24. The shutdown operation described in detail is in this case to be regarded only as an example and can be embodied differently for different medical apparatuses.

The operator console 50, which originally triggered or controlled the shutdown operation of the magnetic resonance apparatus 10, can subsequently likewise perform a self-shutdown by means of its own dedicated shutdown sequence. Said shutdown sequence can include for example an installation of a more recent version of a piece of software (a software update) of the operator console 50 and/or a cleanup of temporary files and/or a shutdown of an operating system of the operator console 50. Subsequently a computer of the operator console 50 can perform a self-shutdown. In this case the shutdown operation of the operator console 50 advantageously comprises placing the operator console 50 into a soft-off state, for example an ACPI S5 soft-off mode.

A startup of the system, in particular a restart after the described shutdown operation, can then be triggered by a user at the second input unit 12. The actuation of the second input unit 12 initially triggers a startup of the magnetic resonance apparatus 10, via the control computer 24 of the magnetic resonance apparatus 10 as intermediary. Subsequently and/or simultaneously, the startup command is forwarded to the operator console 50 via the second interface, which in the case shown in FIG. 2 is embodied as a network interface LAN between the magnetic resonance apparatus 10 and the operator console 50. In the case shown in FIG. 2, the operator console 50 has a Wake-on-LAN interface WOL. Accordingly, the startup command can be forwarded by the network interface LAN to the operator console 50 in such a way that the startup operation of the operator console 50 is triggered by a Wake-on-LAN method. Advantageously, the network interface is in this case embodied in such a way that the startup operation of the magnetic resonance apparatus 10 and the startup operation of the operator console 50 run concurrently.

Figure 3:
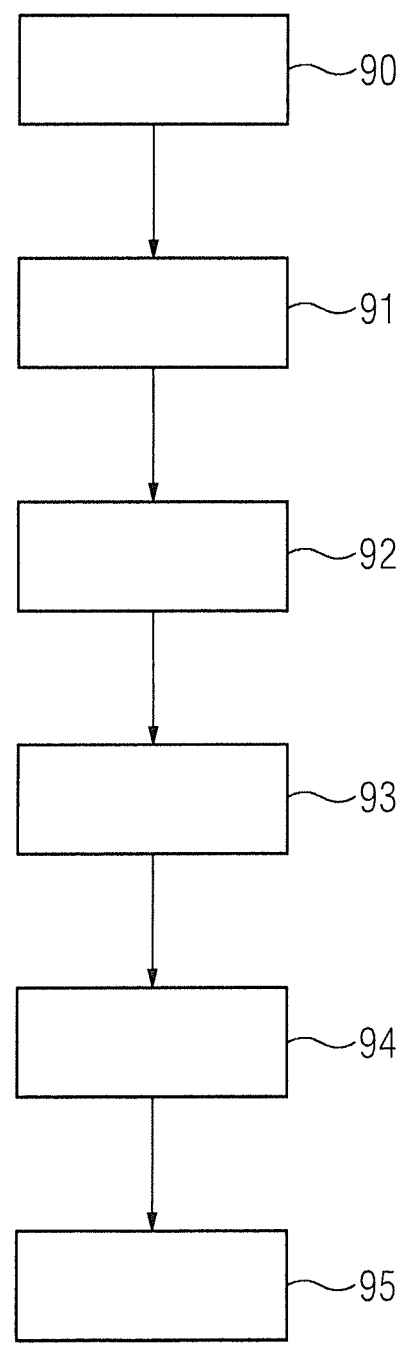
FIG. 3 shows an embodiment of the method according to the invention.

FIG. 3 shows an embodiment variant of an inventive method for controlling a system comprising a medical apparatus and an operator console for operating and controlling the medical apparatus. The method illustrated in FIG. 3 can be developed as deemed appropriate on the basis of the physical features from FIG. 1 or FIG. 2, in which event the physical features can in this case, if necessary, be reformulated as method features.

In a first method step 90, a shutdown command is acquired by means of a first input unit assigned to the operator console.

In a further method step 91, a shutdown operation of the operator console is triggered as a function of the acquired shutdown command.

In a further method step 92, the shutdown command is forwarded from the operator console to the medical apparatus, wherein a shutdown operation of the medical apparatus is triggered.

In a further method step 93, a startup command is acquired by means of a second input unit assigned to the medical apparatus following termination of the shutdown operation of the operator console and of the medical apparatus.

In a further method step 94, a startup operation of the medical apparatus is triggered as a function of the acquired startup command.

In a further method step 95, the startup command is forwarded from the medical apparatus to the operator console, wherein a startup operation of the operator console is triggered.

The method steps of the inventive method illustrated in FIG. 3 can be performed by a computer of the system. For this purpose the computer has requisite software and/or computer programs which are stored in a memory unit of the computer. The software and/or computer programs have program means that are configured to perform the method according to the invention when the computer program and/or the software in the computer are/is executed by a processor unit of the computer.

Although modifications and changes may be suggested by those skilled in the art, it is the intention of the inventors to embody within the patent warranted hereon all changes and modifications as reasonably and properly come within the scope of their contribution to the art.

We claim as our invention:

1. A system comprising:
   a medical apparatus;
   an operator console comprising a console computer configured to operate the medical apparatus at least partially in response to entries made by a user into the console computer;
   a first input processor assigned exclusively to the operator console and configured to acquire a shutdown command that triggers a shutdown operation of the operator console;
   a second input processor assigned exclusively to the medical apparatus and configured to acquire a startup command that triggers a startup operation of the medical device;
   a first interface configured to forward the shutdown command acquired by the first input processor from the operator console to the medical apparatus, with the shutdown command forwarded to the medical apparatus triggering a shutdown operation of the medical apparatus; and
   a second interface configured to forward the startup command acquired by the second input processor from the medical apparatus to the operator console, with the startup command forwarded to the operator console triggering a startup operation of the operator console.

2. A system as claimed in claim 1 wherein said medical apparatus and said operator console are situated at respective locations that are spatially separated from each other, with said medical device situated in an equipment room and the operator console situated in a control room.

3. A system as claimed in claim 1 wherein the medical apparatus comprises an apparatus control computer, and wherein said first interface is configured to forward the shutdown command acquired by the first input unit from the operator console to the apparatus control computer of the medical apparatus.

4. A system as claimed in claim 3 wherein said apparatus control computer is situated in said equipment room.

5. A system as claimed in claim 3 wherein said medical apparatus is connected to a power supply that supplies power to the medical apparatus for operation thereof, and wherein said shutdown apparatus comprises a disconnection of the medical apparatus from the power supply initiated by said apparatus control computer dependent on the shutdown command forwarded to the apparatus control computer from the operator console.

6. A system as claimed in claim 1 wherein said shutdown operation of the operator console comprises placing the operator console in a soft-off state.

7. A system as claimed in claim 1 wherein said second interface is configured as a network interface between said medical apparatus and said operator console, and wherein said startup operation of the operator console is triggered by a Wake-on-LAN method.

8. A system as claimed in claim 1 wherein said second interface is configured to cause said startup operation of the medical apparatus and the startup operation of the operator console to proceed concurrently.

9. A method comprising:
from an operator console comprising a console computer, operating a medical apparatus at least partially in response to entries made by a user into the console computer;
with a first input processor assigned exclusively to the operator console, acquiring a shutdown command that triggers a shutdown operation of the operator console;
with a second input processor assigned exclusively to the medical apparatus acquiring a startup command that triggers a startup operation of the medical device;
forwarding the shutdown command acquired by the first input processor from the operator console to the medical apparatus, with the shutdown command forwarded to the medical apparatus triggering a shutdown operation of the medical apparatus; and
forwarding the startup command acquired by the second input processor from the medical apparatus to the operator console, with the startup command forwarded to the operator console triggering a startup operation of the operator console.

10. A non-transitory, computer-readable data storage medium encoded with programming instructions for controlling a system comprising a medical apparatus, and operator console comprising a console computer configured to operate the medical apparatus at least partially in response to entries made by a user into the console computer, a first input processor assigned exclusively to the operator console, a second input processor assigned exclusively to the medical apparatus, a first interface and a second interface, said programming instructions being distributed among respective memories of said console computer, said first input processor and said second input processor, and said programming instructions causing the first and second input processors and the control computer to:
operate the medical apparatus at least partially in response to entries made by a user into the console computer;
with first input processor assigned exclusively to the operator console, acquire a shutdown command that triggers a shutdown operation of the operator console;
with second input processor assigned exclusively to the medical apparatus, acquire a startup command that triggers a startup operation of the medical device;
forward the shutdown command acquired by the first input processor from the operator console to the medical apparatus, with the shutdown command forwarded to the medical apparatus triggering a shutdown operation of the medical apparatus; and
forward the startup command acquired by the second input processor from the medical apparatus to the operator console, with the startup command forwarded to the operator console triggering a startup operation of the operator console.

* * * * *